(12) United States Patent
Dean et al.

(10) Patent No.: US 7,659,067 B2
(45) Date of Patent: Feb. 9, 2010

(54) METHOD FOR IDENTIFICATION OF MEDICALLY RELEVANT FUNGI

(75) Inventors: Timothy R. Dean, Oxford, ND (US); Michael J. Kohan, Rougemont, NC (US)

(73) Assignee: The United States of America as represented by the Administrator of the U.S. Environmental Protection Agency, Washington, DC (US)

( * ) Notice: Subject to any disclaimer, the term of this patent is extended or adjusted under 35 U.S.C. 154(b) by 252 days.

(21) Appl. No.: 11/355,190

(22) Filed: Feb. 16, 2006

(65) Prior Publication Data

US 2007/0196830 A1    Aug. 23, 2007

(51) Int. Cl.
*C12Q 1/68*    (2006.01)

(52) U.S. Cl. .......................... 435/6; 435/91.1; 435/91.2; 536/24.33

(58) Field of Classification Search ........................ None
See application file for complete search history.

(56) References Cited

U.S. PATENT DOCUMENTS 6,235,890 B1 * 5/2001 Morrison et al. ......... 536/24.33
6,872,523 B1 * 3/2005 Iwen et al. .................... 435/6

OTHER PUBLICATIONS

Wu et al. J. Environ. Monit. vol. 4:377-382. 2002.*
Borneman et al., Applied and Environmental Microbiology vol. 66:4356-4360. 2000.*

\* cited by examiner

*Primary Examiner*—Heather G Calamita
(74) *Attorney, Agent, or Firm*—Hendricks & Assocs.; John Tarcza

(57) ABSTRACT

Multiple species of fungi in an environment can be identified in one sample by extracting and purifying fungal DNA in the sample. PCR is then performed followed by cloning the amplifed DNA and transforming the DNA into bacteria for purposes of growing the organisms. Colonies of the growth containing transformed bacteria are then chosen on the basis of coloration. Plasmids from the chosen colonies were then purified and the DNA is analyzed to identify fungi present in the sample.

15 Claims, No Drawings

METHOD FOR IDENTIFICATION OF MEDICALLY RELEVANT FUNGI

FIELD AND BACKGROUND OF THE INVENTION

This invention relates to a method of screening for medically relevant fungi. In recent years there has been an increase in the awareness of the importance of a healthy indoor environment. A central dynamic affecting the quality of the indoor environment is the control and removal of biological contaminants, mainly the filamentous fungi (mold). Estimates of fungal contamination of homes in North America indicate that up to 40% contain mold growth, while in other parts of the world such as Northern Europe the proportion of fungal contaminated homes ranges between 20-40%. Fungal contaminants that can inundate the indoor environment include microbial volatile organic compounds (MVOC), allergenic proteins, and in some cases mycotoxins.

Adverse health effects that have been attributed to the filamentous fungi include itchy eyes, stuffy nose, fatigue, headache, and in severe cases idiopathic pulmonary hemosiderosis (IPH) in infants resulting in death. The term sick building syndrome accurately reflects the potential that molds can have on the built environment. Currently, only a small percentage of these fungal contaminants have been implicated in adverse health effects. However, with the increased interest and research aimed at these organisms it is probable that the list of organisms that induce ill health will be expanded.

Fungal organisms have historically been identified based on morphological characteristics, both macroscopic and microscopic. Examination of the traits and distinctions of the colonies, and morphological characteristics such as conidial size, texture, shape, and structure are all commonly used methods of identification. Because these methods may require up to two weeks for an identification to be made, these prior art methods are time consuming and highly inaccurate. It is extremely difficult to distinguish between organisms that are similar morphologically. Additionally, not all of the organisms in a sample will be culturable. This inevitably leads to misidentification and understatement of the organisms that constitute the microbial community. Due to these concerns it is imperative that new methods of fungal identification be developed that are rapid, specific, easy to perform, and cost effective. Because of these concerns, there is need for molecular biology techniques that circumvent many of the problems related to morphological identification. Techniques that have proven successful include quantitative Polymerase Chain Reaction (qPCR), restriction fragment length polymorphism (RFLP) analysis, random amplified polymorphic DNA (RAPD) analysis, and image analysis. Each of these methods has been used successfully to identify and/or quantify fungal organisms from a number of different environmental samples. These methods enable rapid, sensitive, and specific identification of fungal organisms, However, in most cases they are only being used to identify single organisms from complex environmental samples. However, fungal organisms found in the environment are rarely if ever encountered singly. A more practical approach is the identification of numerous organisms from a single environmental sample. Identification of multiple fungal species in a single PCR-based reaction would save time and money, while maintaining high specificity and accuracy.

SUMMARY OF THE INVENTION

It is the purpose of this invention to provide means for efficient, economical and reliable means for identifying pathogenic fungi in the environment. The invention utilizes usual methods of extracting and purifying fungal DNA, but extracts DNA from more than one fungi in a sample without culturing the fungi, PCR is then performed followed by cloning the amplified DNA and transforming the DNA into bacteria for purposes of growing the organisms. Colonies of the growth containing transformed bacteria are then chosen on the basis of coloration. In the example, the white colonies were chosen. Plasmids from the chosen colonies were then purified and the DNA was analyzed.

While the method exemplified for extracting DNA was bead beating followed by phenol/chloroform ethanol precipitation methodology, alternate methods including various enzymatic (proteins and keratins) treatments to degrade the fungal spore coat releasing genomic DNA followed by phenol/chloroform ethanol precipitation treatment may be used. Numerous publicly available kits are designed to extract DNA and are readily available on the market. In step 3, the colonies were grown in *E. coli*, the *E. coli* were plated and grown up and the white colonies were chosen. Any standard method of plasmid purification could be used. There are publicly available kits for plasmid purification that can be used to advantage. Hence, the invention is not limited to the particular steps exemplified herein.

The sequence that is exemplified in the detailed description covers the 18S ribosomal RNA gene, through the internal transcribed spacer 1, 5.8S ribosomal RNA gene, internal transcribed spacer 2, and into the 28S ribosomal RNA gene. Each species has a unique nucleotide sequence through this stretch of genes. A single base change can allow the elucidation of a specific species of filamentous fungus. Genetic sequencing of these genes allows one to discern the exact sequence of nucleotides and make comparisons and identifications between organisms.

DETAILED DESCRIPTION OF THE INVENTION

This invention involves combining polymerase chain reaction (PCR) with genetic sequencing to produce a genentic sequence unique to an individual organism, amplifying DNA material using universal fungal primers and PCR techniques, transferring the amplified product into *E coli* cells and identifying the presence of the various fungi types using genetic sequencing methods, cloning amplified DNA material into a host bacteria, culturing the host bacteria, harvesting DNA material from the host bacteria and producing genetic sequences from the harvested DNA material. By sequencing the PCR amplicon from numerous different organisms and developing a database, this procedure can plug environmental sequences into the database for positive identification of limitless fungal organisms. This method has the resolving power to accurately identify organisms at the species level based on the nucleic acid sequence of their ribosomal genes. Other technologies utilize small stretches of nucleic acid sequence for probe binding, but this methodology is based on the sequence of the entire PCR amplified site.

Described herein is a multiplex PCR coupled to cloning and sequencing of the cloned insert that has been developed and optimized. This method as exemplified provides means for identifying four organisms via analysis of the ribosomal DNA sequence. However, the methods of the invention are suitable for identification of many other fungal organisms from a single environmental sample. The object of this design is to optimize a fungal screen capable of identifying numerous medically relevant indoor contaminants. The organisms (*Penicillium purpurogenum, Stachybotrys chartarum, Aspergillus sydowii*, and *Cladosporium cladosporioides*) were all chosen based on their prevalence in buildings contaminated with fungal growth. Research has shown that these organisms can serve as signature species for evaluating indoor environments.

Prior to multiplex reactions each organism was subjected to individual PCR to ensure that sufficient amplification was obtained with little or no spurious product formation and to confirm that the correct sequence was being amplified. Primers ITS-1 and ITS-4 were used to generate amplified ribosomal fragments. These primers amplify from the 18S ribosomal RNA gene, through the internal transcribed spacer 1, 5.8S ribosomal RNA gene, internal transcribed spacer 2, and into the 28S ribosomal RNA gene. All of the fungal strains that were used amplified successfully producing a single PCR product of the desired length, approximately 550-600 base pairs. The resultant PCR products were very clean and did not require additional purification prior to cloning and transformation. Additional sequence analysis was carried out with a thorough search of NCBI (National Center for Biotechnology Information) followed by alignment and analysis with BioEdit software confirming that the proper fragments were being amplified and that the sequences corresponded to the organisms being used in this analysis (Table 1).

| Fungal Isolate | Accession no. | Multiplex Concentration (spores) | Length (bp) |
|---|---|---|---|
| *Penicillium purpurogenum* | AY373926 | $10^5$ | 596 |
| *Stachybotrys chartarum* | AY185565 | $10^6$ | 581 |
| *Aspergillus sydowii* | AY373869 | $10^4$ | 568 |
| *Cladosporium cladosporioides* | AY361968 | $10^5$ | 551 |

Materials and Methods

Fungal Isolates.

*Aspergillus sydowii, Cladosporium cladosporioides*, and *Stachybotrys chartarum* were all kindly provided by Research Triangle Institute (RTI). All of the organisms provided by RTI were environmental isolates obtained from environmental dust samples from houses in Cleveland, Ohio. *Penicillium purpurogenum* was kindly provided by Steve Vesper from EPA/ORD/NERL. It was also isolated from environmental dust samples from houses in Cleveland, Ohio.

Growth and Harvest of Spores.

All fungal organisms were grown on Sabouraud Dextrose Agar (SDA) plates. Plates were prepared according to the suppliers instructions. Each organism was plated and grown to confluence on three different SDA plates in preparation for spore harvest. Organisms were allowed to grow for at least 10 days prior to spore harvest. Spores were harvested as previously reported (Dean, T. R., Betancourt, D., Menetrez, M. Y., (2004) A rapid DNA extraction method for PCR identification of fungal indoor air contaminants. *J Microbiol Methods.* 56:431-434; Crow, S. A., Ahearn, D. G., Noble, J. A., Moyenuddin, M., Price, D. L., (1994) Microbial ecology of buildings: effects of fungi on indoor air quality. *Amer. Environ. Laboratory.* 2:16-18). Spores were harvested from plates with 3 ml of 0.01 M phosphate buffer with 0.05% (v/v) Tween 20 (Sigma Chemical, St. Louis, Mo., USA) by gently agitating the plate surface with a bent glass rod. The supernatant from the three plates was combined and the spore suspension centrifuged at 12,000×g for 5 min. The supernatant was then decanted leaving the spore pellet intact. The pellet was washed three times with 10 ml of phosphate buffer and stored at 4° C. until needed. The total spore counts were enumerated by direct microscopic counting on a hemacytometer as described by Roe et al. (Roe, J. D., Haugland, R. A., Vesper, S. J., Wymer, L. J., (2001) Quantification of *Stachybotrys chartarum* conidia in indoor dust using real time, fluorescent probe-based detection of PCR products. *J. Expo. Anal. Environ. Epidemiol.* 11:12-20).

Fungal DNA Purification.

The spore DNA was purified as previously reported (Dean et al., 2004, supra). The spores were mechanically broken open using a bead milling method followed by a phenol:$CHCl_3$-ethanol precipitation step. For bead milling, 0.25 g of acid-washed glass beads (212-311 μm) were placed in a 2 ml screw cap conical tube. 200 μl or approximately $10^7$ spores were added to the glass beads. The tube was then shaken in a mini bead beater (Biospec Products, Bartlesville, Okla.) for 50 seconds at the maximal rate. The tube was then placed on ice for 1 minute to cool the sample and then shaken a second time. The supernatant was removed from the beads and subjected to a phenol:$CHCl_3$ extraction and an ethanol precipitation (Ausubel, F. M., Brent, R., Kingston, R. E., Moore, D. D., Seidman, J. G., Smith, J. A., Struhl, K., (1994) Phenol: Chloroform Extraction, in: *Current Protocols in Molecular Biology*, John Wiley & Sons, Inc., New York, pp. 2.1.1-2.1.3) Following precipitation the samples were stored at minus 20 EC until needed.

Primers and PCR Conditions.

PCR reactions were carried out using forward primer ITS-1 (5' TCCGTAGGTGAACCTGCGG 3') (Seq. ID No. 1) and reverse primer ITS-4 (5' TCCTCCGCTTATTGATATGC 3') (Seq. ID No. 2). These primers are considered universal fungal primers and have been shown to amplify the organisms used in this study. Initial PCR optimization consisted of obtaining amplification of each target gene under individual reaction conditions (Table 2). These conditions resulted in the exact conditions written below.

TABLE 2

Reaction conditions used in PCR optimization assays.

| Reagent | Initial Concentration | Volume | Final Concentration |
|---|---|---|---|
| 10 dNTPs | 10 mM | 1.0 ml | 0.4 mM |
| 10× Taq Buffer | 10× | 2.5 ml | 1× |
| ITS-1 Primer | 25 mM | 1.0 ml | 1 mM |
| ITS-4 Primer | 25 mM | 1.0 ml | 1 mM |
| Template | Variable | 2.5 ml | Variable |
| $MgCl_2$ | 25 mM | 1.5 ml | 1.5 mM |
| $dH_2O$ | — | 15.35 ml | — |
| Taq Polymerase | 5 U/ml | 0.15 ml | 0.75 U |
| Final Volume | | 25.0 ml | |

In the end, each PCR reaction contained: 0.2 mM each dNTP, 1.5 mM MgCl2, 1.5 U Platinum Taq DNA polymerase, Buffer (50 mM KCl, 10 mM Tris-HCl, pH 9.0 at 25 EC, 0.1% Triton X-100), and variable template concentrations. PCR was performed for 35 cycles of 96 EC 30 sec; 50EC 15 sec; and 68EC 2 min. The PCR products were separated by electrophoresis in 2% low melting point agarose, and visualized by ethidium bromide staining. To confirm that the proper ribosomal sequences were being amplified, each PCR product was sequenced using an ABI 3100 Genetic Analyzer with the output sequences analyzed for accuracy.

Plasmid Construction and Transformation

Plasmids were constructed and *Escherichia coli* DH5α were transformed using the TOPO TA Cloning system (Invitrogen Life Technologies, Carlsbad, Calif.). Reactions were carried out following the manufacturer's protocols. Briefly, 1 µl of the PCR reaction was combined with 3 µl dH$_2$O, 1 µl Invitrogen salt solution, and 1 µl TOPO vector. The constituents were gently mixed and incubated at room temperature for 10 minutes. Following incubation, 2 µl of the reaction mixture was added to 1 vial of one shot cells for transformation. Following gentle mixing the reaction was placed on ice for 30 minutes, followed by a heat shock for 30 seconds at 42 EC. Following heat shock, 250 µl of SOC media were added to the reaction mixture, mixed gently and incubated at 37 EC for 1 hour at 200 rpm. After incubation 10 µl or 50 µl was plated onto Luria-Bertani media (LB media) containing 50 µg/ml kanamycin and 40 µl of 40 mg/ml X-gal in dimethyl formamide. Plates were incubated overnight at 37 EC. Following incubation white colonies were chosen and transferred to LB broth containing 50 µg/ml kanamycin and grown overnight for plasmid harvest. Plasmids were harvested using the QIAprep Spin Miniprep system following the manufacturer's protocols (Qiagen, Inc. Valencia, Calif.).

Sequencing

Genetic sequencing of the amplified ribosomal sequences was carried out utilizing the Big Dye Terminator system (Applied Biosystems, Foster City, Calif.). To ensure that the entire amplified fragment was accurately sequenced, M13 forward (5' GTAAAACGACGGCCAG 3') (Seq. ID No. 3) and reverse (5' CAGGAAACAGCTATGAC 3') (Seq. ID No. 4) primers were used. These primers anneal to locations on the plasmid directly upstream and downstream of the cloning site. Briefly, 1 µl of forward or reverse primer was combined with 4 µl dH$_2$O, 5 µl plasmid template, and 4 µl Big Dye terminator ready reaction mixture and cycled through the same PCR regimen cited above except that only 25 cycles of replication were necessary. Following removal of dye terminators (Micro Bio-Spin P-30 spin columns Bio-Rad Laboratories, Hercules, Calif.) samples were analyzed on an ABI 3100 genetic analyzer (Applied Biosystems, Foster City, Calif.) utilizing ABI Sequencing Analysis Software version 3.7.

Analysis on Gypsum Wallboard

Pieces of gypsum wallboard were cut into coupons measuring 1.5"×3.0"×0.25". In order to make the coupons suitable for fungal growth each piece was wetted with 10 ml sterilized dH$_2$O. After allowing the dH$_2$O to soak into the wallboard, 400 µl of 0.01 M phosphate buffer with 0.05% (v/v) Tween 20 (Sigma Chemical, St. Louis, Mo., USA) containing $10^6$ spores of each *Penicillium purpurogenum, Stachybotrys chartarum, Aspergillus sydowii,* and *Cladosporium cladosporioides* was pipetted into the center of the coupon. The spores were then allowed to grow for 3 weeks at room temperature and 100% relative humidity.

Fungal spores were harvested from the wallboard coupons via mastication and washing. DNA extraction and all subsequent enzymatic manipulations, cloning and sequencing were completed exactly as described as above.

Multiplex PCR reactions were carried out using the exact conditions outlined for successful single PCR reactions. Using the Primers and PCR conditions as described herein gave best results for single reaction/multiplex reactions listed in this section. If individual reactions are carried out using the above conditions amplification will be optimal. The only variables that were adjusted were the template concentrations and the concentration of Taq polymerase. Due to the varying size of the resultant PCR products it was possible to qualitatively judge the presence of all 4 organisms within a multiplex reaction prior to cloning and subsequent sequencing. These variations in size are the result of base deletions and substitutions throughout the amplified region. When observed on an agarose gel following electrophoresis the differences in size/mobility allow for a qualitative judgment. These sequence lengths are noted in table 2.

Due to different amplification efficiencies the template concentrations were important variables in generating all 4 fragments in a single reaction. *A. sydowii* seemed to amplify with the greatest efficiency and required the greatest dilution down to the equivalent of $10^4$ spores per reaction. *C. cladosporioides* and *P. purpurogenum* both generated good product amplification at $10^5$ spores per reaction. *S. chartarum* seemed to amplify with the least efficiency. It was found that $10^6$ spores per reaction were required for sufficient product generation in the presence of the other organisms. It is also possible that differences in ribosomal DNA copy number impact amplification from the different organisms allowing certain organisms to out compete other members in the same reaction.

Shifting from single PCR to multiplex PCR reactions also required an increase in the concentration of Taq polymerase necessary for robust product generation (data not shown). Individual reactions required 0.75 units of Taq polymerase for amplification, while multiplex reactions required 1.5 units of Taq polymerase for robust product generation of all 4 reaction templates. This increase is most likely due to the increase in the amount of total template and the competition generated between these different template copies.

Individual PCR reactions were cloned into the TOPO TA Cloning system and subsequently sequenced to ensure that each organism was amenable to the procedure. Initial sequencing reactions using either ITS-1 or ITS-4 produced usable sequence data. However, while the middle of the sequence read was very robust, both the 5' and 3' ends of the fragment decreased in sequencing efficiency. To compensate for the decrease in efficiency at the ends of the sequence all cloned products were sequenced using both the M13 forward and reverse primers. These primers anneal outside of the cloning site and allowed for accurate base calls throughout the entire cloned fragment. This increase in sequencing efficiency allowed for unambiguous species identification to be made with each organism based on sequence data.

Multiplex reactions were completed and cloned into the plasmid vector. The goal was to obtain sequence data for all 4 organisms by analyzing 10% or less of the white (transformed) colonies. Table 3 clearly shows the differences that occurred when different concentrations of initial template were used. When each organism was present in the multiplex reaction at $10^5$ spores it was possible to identify all 4 fungal species based on the resultant sequence data. However, the distribution was heavily skewed toward *A. sydowii*, which was present in 11 of 18 clones. By adjusting the initial concentrations of template for each of the organisms it was possible to generate a fairly even distribution of clones (Table 3).

TABLE 3

| Organism | Spore Conc. | # of Clones | Spore Conc. | # of Clones | Total # Clones |
| --- | --- | --- | --- | --- | --- |
| C. cladosporioides | $10^5$ | 3 | $10^5$ | 6 | 9 |
| S. chartarum | $10^5$ | 3 | $10^6$ | 6 | 9 |

TABLE 3-continued

| Organism | Spore Conc. | # of Clones | Spore Conc. | # of Clones | Total # Clones |
|---|---|---|---|---|---|
| P. purpurogenum | $10^5$ | 1 | $10^5$ | 5 | 6 |
| A. sydowii | $10^5$ | 11 | $10^4$ | 2 | 13 |

Results:

In order to test this methodology in a real world application small pieces of gypsum wall board were wetted with $dH_2O$ and inoculated with $10^6$ of each *Penicillium purpurogenum, Stachybotrys chartarum, Aspergillus sydowii*, and *Cladosporium cladosporioides*. After allowing the fungi to grow on the wallboard for a 3 week period, it was visually observed that the surface was completely covered with fungal growth. Due to the morphological characteristics of the fungal growth it was visually determined that *S. chartarum* was the dominant species present. It was at this point that the spores were harvested from the building material and subjected to sequencing analysis.

Previously it was shown that a very successful method of extracting fungal material from building materials (wallboard, ceiling tile, etc.) is the use of a masticator blender. Due to the visual growth characteristics noted above, following fungal extraction from the gypsum board a microscopic comparison was made of the spores. This comparison confirmed that the predominant spore present in the mixture was *Stachybotrys*. This was not a surprising result because the environmental conditions in which the spores were allowed to grow (heavy initial wetting and 100% relative humidity) favored *Stachybotrys*.

Sequencing analysis involved comparison between published sequences and sequences derived from the experiments and also showed that the predominant species extracted from the gypsum board was *Stachybotrys chartarum*. *S. chartarum* accounted for 17 of the 20 clones analyzed, while *A. sydowii* accounted for 2 clones and *C. cladosporioides* accounted for a single clone. *P. purpurogenum* did not show up in the analysis. It is believed that more natural growth conditions with varying levels of relative humidity and wetting would result in a more representative fungal culture, however, the identification of both *A. sydowii* and *C. cladosporioides*, as underrepresented members of the fungal culture, clearly shows that the resolving power of the methodology is sufficient to give an accurate fungal contaminant screen in the indoor environment.

The upside of this method is the potential to identify unlimited numbers of organisms, positive identifications being limited by the number of clones analyzed. This application in fungal screening in the indoor built environment may also be used for air sampling as well as surface analysis allowing for a more complete picture of the level of contamination in an indoor space.

What we claim is:

1. A multiplex method of identifying multiple species of fungi from fungal spores in an environmental sample containing a mixture of multiple species of fungi comprising the steps of:
   1) extracting and purifying multiple different fungal genomic DNA from fungal spores in the sample simultaneously by a means that would allow for downstream enzymatic reactions, without culturing the fungi;
   2) performing a PCR reaction utilizing universal primers;
   3) cloning amplified DNA and transforming into bacteria, then plating, culturing bacteria and choosing the transformed colonies;
   4) purifying plasmids from bacteria and sequencing the amplified DNA; then
   5) analyzing sequence data to determine specific organisms present in the sample.

2. The method of claim 1 wherein, in step 3, the DNA is transformed into *E. coli*.

3. The method of claim 1 wherein all cloned products are sequenced using both forward and reverse primers.

4. The method of claim 1 wherein the amplified DNA is about 550 to 600 base pairs.

5. The method of claim 1 wherein the DNA is extracted using bead beating followed by solvent extraction.

6. The method of claim 1 wherein at least one of the fungi are selected from the group consisting of *Penicillium purpurogenum, Stachybotiys chartarum, Aspergillus sydowii* and *Cladosporium cladosporioides*.

7. The method of claim 1 wherein one of the universal primers in step 2 has the sequence of SEQ ID NO:1 or SEQ ID NO:2.

8. A method of identifying multiple species of fungi from fungal spores in an environmental sample without culturing the fungi comprising the steps of:
   1) obtaining an environmental sample suspected of containing fungi,
   2) extracting and purifying multiple fungal genomic DNA from fungal spores in the sample without culturing the fungi by a means that would allow for downstream enzymatic reactions;
   3) amplifying the DNA by a PCR reaction utilizing universal primers to obtain amplified DNA;
   4) sequencing the amplified DNA; and
   5) analyzing sequence data to determine specific organisms present in the sample.

9. The method of claim 8 wherein, in step 2, the DNA is extracted by mechanically breaking open the fungal spores to release genomic DNA followed by solvent extraction.

10. The method of claim 8 wherein at least one of the fungi are selected from the group consisting of *Penicillium purpurogenum, Stachybotrys chartarum, Aspergillus sydowii* and *Cladosporium cladosporioides*.

11. The method of claim 8 wherein one of the universal primers in step 2 has the sequence of SEQ ID NO:1 or SEQ ID NO:2.

12. The method of claim 1 wherein the environmental sample is an indoor air.

13. The method of claim 1 wherein the environmental sample is an indoor wallboard.

14. The method of claim 8 wherein the environmental sample is an indoor air.

15. The method of claim 8 wherein the environmental sample is an indoor wallboard.

* * * * *

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tccgtaggtg aacctgcgg                                                    19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcctccgctt attgatatgc                                                   20

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtaaaacgac ggccag                                                       16

```
<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caggaaacag ctatgac                                                        17
```